(12) United States Patent
Mineur

(10) Patent No.: US 7,439,339 B2
(45) Date of Patent: Oct. 21, 2008

(54) AZO COUPLING REACTIONS OF HYDROPHOBIC COMPOUNDS

(75) Inventor: Catherine Mineur, Macedon, NY (US)

(73) Assignee: Eastman Kodak Company, Rochester, NY (US)

( * ) Notice: Subject to any disclaimer, the term of this patent is extended or adjusted under 35 U.S.C. 154(b) by 348 days.

(21) Appl. No.: 11/109,388

(22) Filed: Apr. 19, 2005

(65) Prior Publication Data

US 2006/0235227 A1    Oct. 19, 2006

(51) Int. Cl.
  *C09B 41/00* (2006.01)

(52) U.S. Cl. .................................................. 534/581
(58) Field of Classification Search ................ 534/581
  See application file for complete search history.

(56) References Cited

FOREIGN PATENT DOCUMENTS

DE            242 050            1/1987

*Primary Examiner*—Fiona T Powers
(74) *Attorney, Agent, or Firm*—Arthur E. Kluegel

(57) ABSTRACT

A process for forming a diazo compound comprises reacting an organic compound bearing an acidic hydrogen with an aryl-diazonium salt in the presence of an inorganic base and a non-halogenated solvent. The process is simpler and more environmentally friendly than known processes.

16 Claims, No Drawings

AZO COUPLING REACTIONS OF HYDROPHOBIC COMPOUNDS

FIELD OF THE INVENTION

This invention relates to a method of preparing azo compounds of hydrophobic compounds such as photographic couplers in a biphasic mixture, in a simple, efficient, environmentally benign and cost-effective way.

BACKGROUND OF THE INVENTION

It is known in the art that some compounds of formula I are useful photographic dyes or dye-forming couplers. Particularly, some of these compounds act as masking couplers. Examples can be found in U.S. Pat. No. 5,466,568 and DE 3530357. The product compounds may be represented by Formula I $$Ar\!-\!N\!=\!N\!-\!R \qquad (I)$$

The compounds of formula I are most commonly prepared by reacting an aqueous diazonium salt, whose preparation in an acidic aqueous mixture, by reacting an amine compound with a nitrite compound, is well-known in the art (see Practical Organic Chemistry, A. I. Vogel) with a hydrophobic coupler moiety in the presence of pyridine, sometimes in the presence of an organic solvent, as shown in Scheme 1. Examples are U.S. Pat. Nos. 5,622,818; 6,132,943; DE 2706117.

Scheme 1

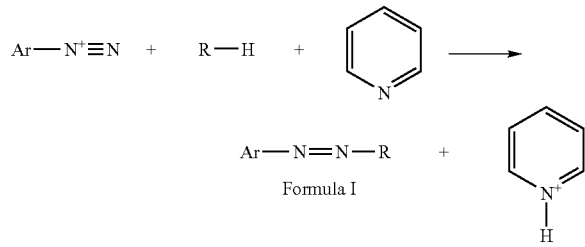

These syntheses suffer from a few drawbacks, first of all in order to promote the azo coupling reaction, they all use pyridine, sometimes in a large excess, which is an expensive, foul-smelling and hazardous volatile organic compound, and which requires treatment of the hazardous waste. Also, they require a multiple-reactor setup, where one reactor is used for the making of the diazonium salt solution, and the second reactor is used for the azo coupling, requiring a transfer of the diazonium salt solution from the first reactor to the second one.

There have been some efforts to use more environmentally-friendly bases, such as some inorganic bases, such as the carbonates, bicarbonates, acetates or hydroxides of alkaline or alkaline-earth metals for making azo compounds. Examples can be found in [Ellwood, M.; Griffiths, J.; Gregory, P. J. C. S. Chem. Comm., 181-183 (1980); Iwamoto, H.; Yoshimura, M.; Sonoda, T.; Kobayashi, H. Bull. Chem. Soc. Jpn, 56, 796-801 (1983); Hashida, Y.; Kubota, K.; Sekiguchi, S. Bull. Chem. Soc. Jpn, 61, 905-909 (1988); Iwamoto, H.; Kobayashi, H.; Murer, P.; Sonoda, T.; Zollinger, H. Bull. Chem. Soc. Jpn, 66, 2590-2602 (1993)]. Examples of actual photographic couplers prepared under these conditions can be found in DD 242050 and examples of azo dyestuff prepared under the same conditions can be found in EP 0028464.

However, in all these cases, the organic solvents most often used were chlorinated solvents (also known hazardous volatile organic compounds), such as methylene chloride or chloroform, and the azo coupling reaction under these biphasic conditions proceeded only if in the presence of a phase-transfer catalyst. Also, the equipment requirement here was again a multi-reactor set-up.

It remains a problem to be solved to have an easy, efficient and cost-effective, while more environmentally responsible, synthesis of azo compounds from hydrophobic couplers.

SUMMARY OF THE INVENTION

The invention provides a process for forming a diazo compound comprising reacting an organic compound bearing an acidic hydrogen with an aromatic-diazonium salt in the presence of an inorganic base and a non-halogenated solvent.

The invention provides a finished product in a simpler and more environmentally friendly way than the known methods.

DETAILED DESCRIPTION OF THE INVENTION

The invention is summarized above. This invention aims to provide a simple and efficient procedure to prepare azo compound derivatives of hydrophobic compounds, using sustainable reagents and solvents, such as inorganic bases and non-chlorinated organic solvents.

The diazotization of the amine compound may be carried out by methods conventionally used for this reaction. For example, sodium nitrite optionally in the form of an aqueous solution thereof may be added to a solution or dispersion of the amine in a strong inorganic acid or an aqueous solution thereof, or to a solution of the amine in acetic acid optionally in a mixture with propionic acid, or by stirring the amine with nitrosyl-sulfuric acid.

The diazonium salt solution, the coupler, the non-chlorinated solvent and the inorganic base are stirred together at a temperature below 25° C. The product of Formula I is isolated from the mixture by any conventional means.

Preferably, the compound, the non-chlorinated solvent and the inorganic base are sequentially added to the vigorously stirred diazonium salt solution at a temperature below 15° C. If desired, the progress of the reaction can be followed by HPLC, or any other suitable analytical means. The mixture can be acidified, the product of Formula I isolated by any conventional means.

Most preferably, the hydrophobic compound and the non-chlorinated solvent are sequentially added to the vigorously stirred chilled diazonium salt solution. The inorganic base is then added in such a way that the reaction mixture is not allowed to warm to 15° C. or above. When the reaction is substantially complete, the compound of Formula I can be isolated from the reaction mixture by for example acidifying the reaction mixture and separating the compound of Formula I from the inorganic salts with aqueous washes or other conventional means, then distilling the organic non-chlorinated solvent (which may be re-used), and crystallizing the compound of Formula I in an organic solvent or a mixture thereof.

The hydrophobic compounds, R—H, are compounds that bear an acidic hydrogen on a hydrophobic residue (typically having log P of 4 or more and usually 6 or more) and that can be activated in the presence of a base allowing them to react and couple with a nucleophilic diazonium salt (Ar—$N_2^+X^-$) and are defined as follows:

A hydrophobic coupler comprises one selected from the group consisting of pyrazolone compounds, phenol compounds, naphthol compounds, such as described as following:

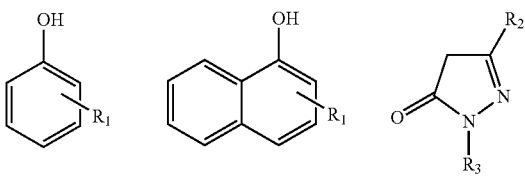

$R_1$ being defined as halogen or one of the following groups: acylamino, carbamoyl, alkyl, alkoxy group, bearing further substitution such as aryl, alkyl, heteroaryl.

$R_2$ being defined as alkyl, acylamino, anilino, alkylamino, dialkylamino, ureido, alkoxy, further substituted by one or more of the following, which may be the same or different: halogen, amido.

$R_3$ being defined as aryl, or heteroaryl, substituted by more than one of the following group, which may be the same or different: alkyl, alkoxy, aryloxy, halogen.

The hydrophobic coupler R—H is preferably one of the following group:

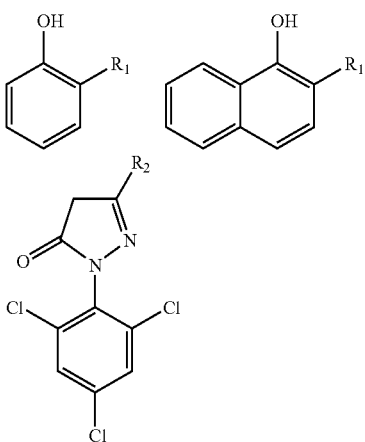

$R_1$ represents an ortho substituent group, such as acylamino.
$R_2$ is defined as above.

The preferred embodiment of hydrophobic coupler R—H comprises one selected from the group consisting of pyrazolone compounds.

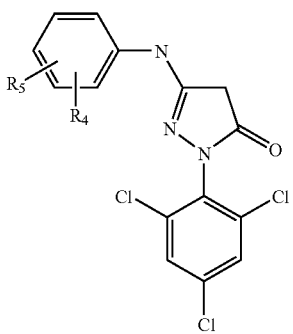

$R_3$, $R_4$ represent an alk, alkoxy, aryloxy, halogeno, acylamino, sulfoamido, with $R_3 \neq R_4$.

The diazonium salt Ar—$N_2^+X^-$ is defined as follows:

Ar represents an aryl or a heteroaryl group substituted by one or more of the following groups, which may be the same or different: alkyl, dialkylamino, amido, acylamino, alkylsulfonamido, arylsulfonamido, alkylsulfo, acyl, sulfonate, thio, mercapto, nitro, cyano, carbamoyl, hydroxyl, alkoxy, aryloxy Ar preferably represents an aryl group substituted by one hydroxyl or one alkoxy group, and by one of the following group (which may be the same or different): H, alkyl, alkoxy, aryloxy, amido, alkylsulfonamido, arylsulfonamido.

The most preferred embodiment is Ar representing a phenyl group substituted by one hydroxyl group or one alkoxy group, and by one of the following groups: H, alkyl, aryloxy, alkoxy, the alkoxy groups being the same or different. In all cases, $X^-$ represents an anion.

The inorganic base comprises one from the group of alkali metal or alkaline-earth salts. Preferably, the inorganic base comprises one of the following: alkali metal or alkaline-earth hydroxide, bicarbonate, carbonate, or acetate. The preferred embodiment of the inorganic base comprises one of the following: sodium hydroxide, sodium acetate, sodium carbonate, sodium bicarbonate, which is used either as an aqueous solution or as a solid. Suitably, the reaction mixture is substantially free of organic bases.

The non-chlorinated solvent comprises any aprotic solvent such as those described in [Solvents and Solvent Effects in Organic Chemistry, Reichardt, R.; pp 66 and 76, VCH (NY), ISBN 0-89573-661-6]. The non-chlorinated aprotic solvent preferably comprises one of the following (being used pure or mixed with one another): toluene, benzene, ethylbenzene, xylene, diethyl ether, di-isopropyl ether, tetrahydrofuran, 1,4-dioxane, ethyl acetate, propyl acetate, acetone, butanone, or nitromethane. The most preferred embodiment of non-chlorinated solvent comprises at least one of the following: toluene, benzene, xylene, ethyl acetate, propyl acetate, acetone, or butanone Unless otherwise specifically stated, use of the term "substituted" or "substituent" means any group or atom other than hydrogen. Unless otherwise provided, when a group, compound or formula containing a substitutable hydrogen is referred to, it is also intended to encompass not only the unsubstituted form, but also form further substituted with any substituent group or groups as herein mentioned, so long as the substituent does not destroy properties necessary for utility. Suitably, a substituent group may be halogen or may be bonded to the remainder of the molecule by an atom of carbon, silicon, oxygen, nitrogen, phosphorous, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy)propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecy-lureido, N-hexadecylureido, N,N-dioctadecylureido, N,N-dioctyl-N'-ethylureido, N-phenylureido, N,N-diphenylure-ido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfona-mido, benzenesulfonamido, p-tolylsulfonamido, p-dodecyl-benzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as pyridyl, thienyl, furyl, azolyl, thiazolyl, oxazolyl, imidazolyl, pyrazolyl, pyrazinyl, pyrimidinyl, pyrolidinonyl, quinolinyl, isoquinolinyl, 2-furyl, 2-thienyl, 2-benzimidazolyloxy or 2-benzothiazolyl; quaternary ammonium, such as triethylammonium; and silyloxy, such as trimethylsilyloxy. If desired, the substituents may themselves be further substituted one or more times with the described substituent groups.

EXAMPLES

In the following are described the preparation of some representative compounds of Formula I

Example 1

Compound of Formula I, from Diazonium D1, and Coupler C1

To the diazonium salt D1 solution prepared from 6.4 Kg of 2-amino-p-cresol, 15.6 gal of water, 13.9 Kg of 37% hydrochloric acid, 3.8 Kg of sodium nitrite, 342 g of urea, at 0-5° C., was added 52 Kg of ethyl acetate, 37.9 Kg of Coupler C1. Then, 9.1 Kg of 50% aqueous solution of sodium hydroxide was added over 45 minutes, at 0-5° C. The resulting mixture was stirred an additional 2 hours at 0-5° C., diluted with 70 Kg of methyl ethyl ketone, and 55 Kg of toluene, and washed twice with 40 gal of water and 7.2 Kg of 37% hydrochloric acid at 55° C., once with 40 gal water. The final organic layer was clarified and concentrated under vacuum, dried by azeotropic toluene distillation. The residue was suspended in 200 Kg of methanol and stirred at 55° C. for 3 h, cooled to 5° C. and collected in a filter box, rinsed with methanol and dried at 50° C. in a vacuum-oven. 40.0 Kg of material were recovered (90% of theoretical yield), in a 99.7 A% assay by LC.

Example 2

Compound of Formula I, from Diazonium D1, and Coupler C1

To the diazonium salt D1 solution prepared from 8.8 Kg of 2-amino-p-cresol, 20.7 gal of water, 17.6 Kg of 37% hydrochloric acid, 5.4 Kg of sodium nitrite, 600 g of urea, at 0-5° C., was added 67 Kg of chilled methyl ethyl ketone, 50 Kg of Coupler C1. Then 11.6 Kg of 50% aqueous solution of sodium hydroxide were added over 20 minutes, at 3-11° C. The resulting mixture was stirred at 0-5° C. for an additional 3 h, diluted with 80 Kg of methyl ethyl ketone, washed twice with 22 gal of water and 10 Kg of 37% hydrochloric acid at 65° C., once with 700 g of EDTA and 300 g of citric acid in 22 gal of water, once with 22 gal of water. The final organic layer was diluted with 80 Kg of methyl ethyl ketone, clarified and concentrated under vacuum, dried by an azeotropic distillation of toluene. The residue was suspended in 151 Kg of methanol, 36 Kg of toluene, 11 Kg of methyl ethyl ketone at 55° C. for 3 h, cooled to 25° C., collected in a filter box, rinsed with 70 Kg of methanol, dried at 50° C. in a vacuum-oven. 50.5 Kg of material were recovered (86% of theoretical yield), in a 99.7 A % assay by LC.

Example 3

Compound of Formula I, from Diazonium D2, and Coupler C1

To the diazonium salt D2 solution prepared from 10.84 g of 3,4-dimethoxyaniline, 80 mL water, 18.42 g of 37% hydrochloric acid, 5.27 g of sodium nitrite, 0.42 g of urea, at 0-3° C., was added 80 mL of chilled ethyl acetate, 50.0 g of Coupler C1. Then 12.0 g of 50% aqueous solution of sodium hydroxide were added over 20 minutes at 0-5° C. The resulting mixture was stirred for 15 h, while the temperature was slowly raised to 20° C., then it was diluted with 200 mL of toluene, and washed twice with 350 mL of water and 8 mL of 37% hydrochloric acid, at 50° C., with 250 mL of water. The final organic layer was clarified, concentrated to an oil, which was dried by a toluene azeotropic distillation and recrystallized from ethanol, dried. 36.53 g (76.5% of theoretical yield) of material were recovered in a 99.5 A % assay by LC.

Example 4

Compound of Formula I, from Diazonium D1, and Coupler C1

To the diazonium salt D1 solution prepared from 6.39 g of 2-amino-p-cresol, 90 mL water, 13.1 g of 37% hydrochloric acid, 3.68 g of sodium nitrite, at 0-3° C., was added 80 mL of ethyl acetate, 39.5 g of Coupler C1. Then 20.3 g of sodium hydrogenocarbonate were added by portions at 0-3° C. The resulting mixture was stirred for 2 h at 0-3° C., then at 20° C. for 15 h. The organic layer was separated at 55° C., washed once with water, concentrated under vacuum, azeotropically dried by toluene distillation, suspended in 100 mL of methanol at 50° C., cooled to 20° C., collected, rinsed with methanol, and dried at 50° C. in a vacuum-oven to a recovered 34.0 g (73% of theoretical yield).

Example 5

Compound of Formula I, from Diazonium D1, and Coupler C1

To the diazonium salt D1 solution prepared from 6.43 g of 2-amino-p-cresol, 85 mL water, 13.1 g of 37% hydrochloric acid, 3.68 g of sodium nitrite, at 0-3° C., were added 80 mL of toluene and 35.9 g of Coupler C1. 10.2 g of 50% aqueous solution of sodium hydroxide was added at 0-5° C. The resulting mixture was stirred at 0-5° C. for 2 h, diluted with 250 mL ethyl acetate and washed at 55° C. twice with 70 mL of water with 4 mL of 37% of hydrochloric acid, then with 140 mL of water. The final organic layer was concentrated, and the residue suspended in a mixture of 200 mL of methanol, 100 mL of water and 5 mL of toluene at 55° C., cooled to 10° C. and collected, rinsed with methanol-water, then water, dried at 50° C. in a vacuum-oven to a recovered 40.9 g (97.4% of theoretical yield).

Some Representative Compounds of Diazonium, Coupler, and Formula I:

| Diazonium | Coupler | Formula I |
|---|---|---|

| Diazonium | Coupler | Formula I |
|---|---|---|
| D3 | C1 | (structure) |
| D1 | C2 | (structure) |

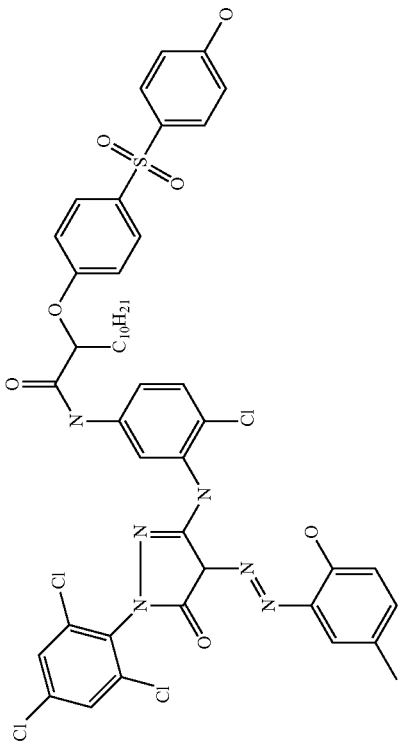

-continued

| Diazonium | Coupler | Formula I |
|---|---|---|
| D1 | C2 | |
| D3 | C4 | |

| Diazonium | Coupler | Formula I |
|---|---|---|
| D1 | C5 | |
| D1 | C6 | |

-continued

| Diazonium | Coupler | Formula I |
|---|---|---|
| D4 (4-methoxybenzene diazonium) | C6 | 1-hydroxy-N,N-di(C18H37)-4-[(4-methoxyphenyl)azo]-2-naphthamide |
| D1 | C7 | 1-hydroxy-N-[4-(3-methylphenoxy)butyl]-4-[(2-hydroxy-5-methylphenyl)azo]-2-naphthamide |

-continued
| Diazonium | Coupler | Formula I |
|---|---|---|
| D1 | 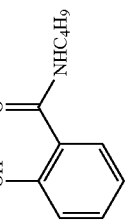 C8 | 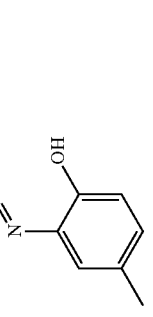 |
| D1 | 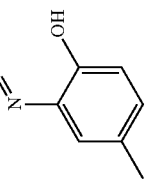 C9 | 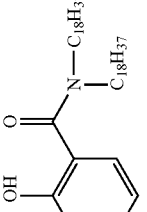 |

The patents and other publications referred to herein are hereby incorporated by reference. The invention has been described in detail with particular reference to certain preferred embodiments thereof, but it will be understood that variations and modifications can be effected within the spirit and scope of the invention.

What is claimed is:

1. A process for forming a diazo compound comprising reacting a mixture consisting essentially of an organic compound bearing an acidic hydrogen with an aromatic-diazonium salt in aqueous solution in the presence of an inorganic base and a non-halogenated organic solvent in accordance with the equation:

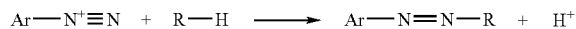

RH being defined as one of the following:

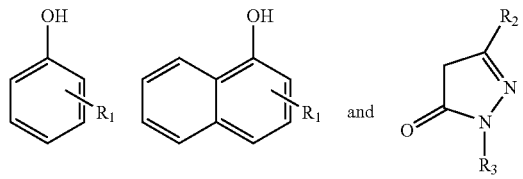

wherein
$R_1$ is selected from the group consisting of halogen, acylamino, carbamoyl, alkyl, and alkoxy groups, which may be further substituted;
$R_2$ is selected from the group consisting of alkyl, acylanino, anilino, alkylamino, dialkylamino, ureido, alkoxy group, which bears further substitution such as an aryl or heteroaryl group, further substituted by alkyl, alkoxy, aryloxy, halogeno, acylamino, and sulfoamido groups;
$R_3$ is selected from the group consisting of aryl and heteroaryl groups; and
Ar is an aromatic group,
wherein the reaction mixture is free of phase transfer catalyst.

2. The process of claim 1 wherein the inorganic base is selected from the group consisting of alkali metal and alkaline earth salts or hydroxides.

3. The process of claim 2 wherein the inorganic base is selected from the group consisting of sodium hydroxide, sodium acetate, sodium carbonate, and sodium bicarbonate.

4. The process of claim 1 wherein the non-halogenated organic solvent is an aprotic solvent.

5. The process of claim 4 wherein the aprotic solvent is selected from the group consisting of toluene, benzene, ethylbenzene, xylene, diethyl ether, di-isopropyl ether, tetrahydrofuran, 1,4-dioxane, ethyl acetate, propyl acetate, acetone, butanone, and nitromethane.

6. The process of claim 5 wherein the non-halogenated organic solvent is selected from the group consisting of benzene, toluene, xylene, acetone, butanone, ethyl acetate, and propyl acetate.

7. The process of claim 1 wherein the aromatic diazonium salt is selected from the group consisting of aryl or heteroaryl, substituted with one or more of the following group, which may be the same or different: alkyl, dialkylamino, acylamino, alkylsulfonamido, arylsulfonamido, ailcylsulfo, acyl, sulfonate, mercapto, nitro, cyano, carbamoyl, hydroxyl, alkoxy, and aryloxy.

8. The process of claim 1 wherein the aromatic diazonium salt is selected from the group consisting of aryl or heteroaryl groups, substituted with an alkoxy or a hydroxyl group, and by one of the following groups: H, alkyl, alkoxy, and hydroxyl groups, the alkoxy groups being the same or different.

9. The process of claim 1 wherein the compound with an acidic hydrogen is a substituted pyrazolone compound having the formula:

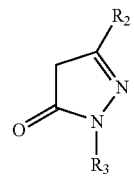

wherein $R_2$ is selected from the group consisting of alkyl, acylamino, anilino, alkylamino, dialkylamino, ureido, alkoxy group, which bears further substitution such as an aryl or heteroaryl group, further substituted by alkyl, alkoxy, aryloxy, halogeno, acylamino, and sulfoamido groups; and $R_3$ is selected from the group consisting of aryl and heteroaryl groups.

10. The process of claim 1 wherein the reaction is represented by the equation (III):

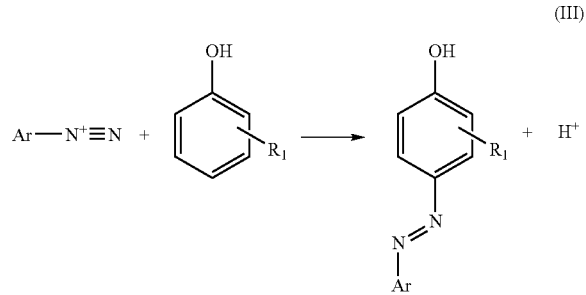

Formula I wherein $R_1$ represents an ortho substituent and Ar is an aromatic group.

11. The process of claim 1 wherein the reaction is represented by the equation (IV):

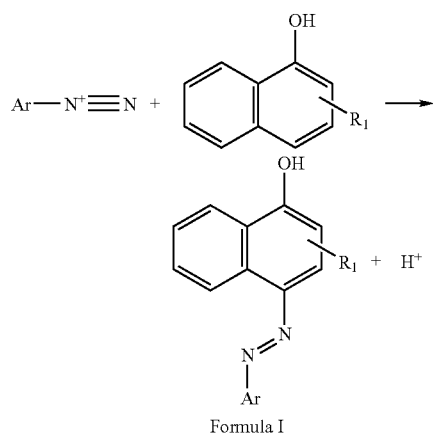

Formula I wherein R₁ represents an ortho substituent and Ar is an aromatic group.

12. The process of claim 1 wherein the reaction is represented by the equation (V):

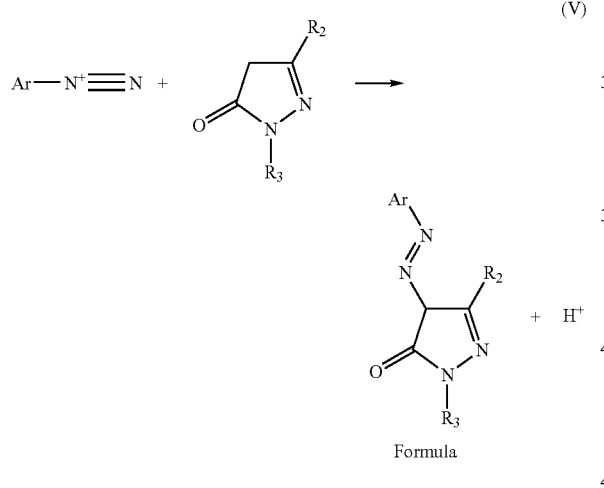

Formula $R_2$ represents an alkyl, acylamino, anilino, alkylamino, dialkylamino, ureido, or alkoxy group;
$R_3$ represents an aryl or heteroaryl group; and
Ar represents an aromatic group.

13. The process of claim 1 wherein the reaction is represented by the equation (VI):

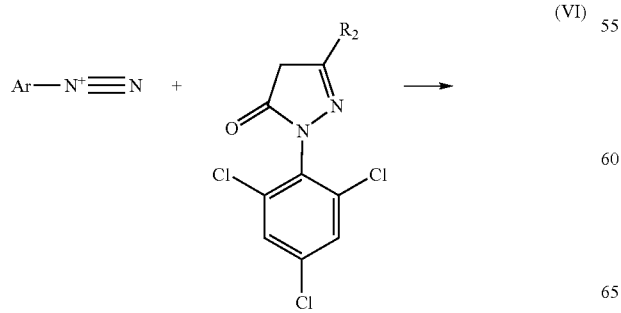

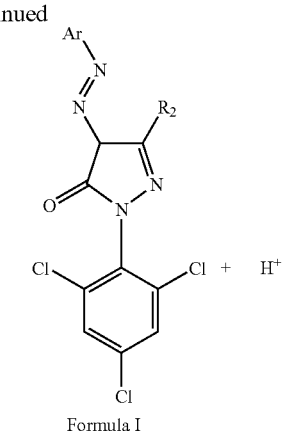

Formula I wherein Ar is an aromatic group and $R_2$ represents an alkyl, acylamino, anilino, alkylamino, dialkylamino, ureido, or alkoxy group.

14. The process of claim 1 wherein the temperature of the reaction is maintained below 15° C.

15. A process for forming a diazo compound comprising reacting an organic compound bearing an acidic hydrogen with an aromatic-diazonium salt in aqueous solution in the presence of an inorganic base and a non-halogenated organic solvent in accordance with the equation:

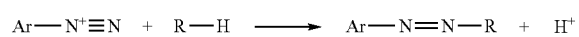

RH being defined as one of the following:

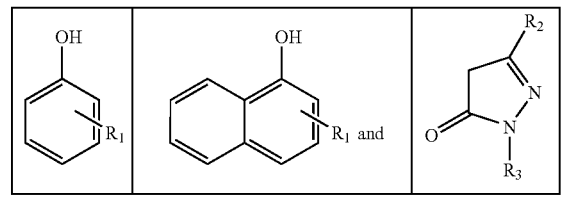

wherein
$R_1$ is selected from the group consisting of halogen, acylamino, carbamoyl, alkyl, and alkoxy groups, which may be further substituted;
$R_2$ is selected from the group consisting of alkyl, acylamino, anilino, alkylamino, dialkylamino, ureido, alkoxy group, which bears further substitution such as an aryl or heteroaryl group, further substituted by alkyl, alkoxy, aryloxy, halogeno, acylamino, and sulfoamido groups;
$R_3$ is selected from the group consisting of aryl and heteroaryl groups; and
Ar is an aromatic group wherein the aryl-diazonium compound is chilled, and
wherein the aqueous solution is free of phase transfer catalyst.

16. The process of claim 1 comprising the further subsequent step of acidifying the reaction product and water washing to remove undesired salts from the product.

* * * * *